United States Patent
Downs, III et al.

(10) Patent No.: US 7,621,871 B2
(45) Date of Patent: Nov. 24, 2009

(54) SYSTEMS AND METHODS FOR MONITORING AND EVALUATING INDIVIDUAL PERFORMANCE

(75) Inventors: J. Hunter Downs, III, Honolulu, HI (US); Traci H. Downs, Honolulu, HI (US); J Patrick Stautzenberger, Haleiwa, HI (US); Erin Nishimura, Honolulu, HI (US); Jason Akagi, Waimanalo, HI (US); Brendan F. P. O'Donnell, Honolulu, HI (US); Fahrettin Olcay Cirit, Honolulu, HI (US); Evan D. Rapoport, Honolulu, HI (US)

(73) Assignee: Archinoetics, LLC, Honolulu, HI (US)

( * ) Notice: Subject to any disclaimer, the term of this patent is extended or adjusted under 35 U.S.C. 154(b) by 302 days.

(21) Appl. No.: 11/424,742

(22) Filed: Jun. 16, 2006

(65) Prior Publication Data
US 2007/0293731 A1    Dec. 20, 2007

(51) Int. Cl.
*A61B 5/00* (2006.01)

(52) U.S. Cl. ...................................................... 600/300

(58) Field of Classification Search ............ None
See application file for complete search history.

(56) References Cited

U.S. PATENT DOCUMENTS

| | | | |
|---|---|---|---|
| 6,530,884 B2 * | 3/2003 | Balkin et al. ............ 600/300 |
| 2002/0005784 A1 | 1/2002 | Balkin et al. |
| 2003/0166558 A1 | 9/2003 | Frangione et al. |
| 2004/0082862 A1 | 4/2004 | Chance |
| 2005/0053904 A1 * | 3/2005 | Shephard et al. ......... 434/236 |
| 2005/0177031 A1 * | 8/2005 | Hursh .................. 600/300 |
| 2005/0215889 A1 | 9/2005 | Patterson, II |
| 2005/0282911 A1 | 12/2005 | Hakkarainen et al. |

* cited by examiner

*Primary Examiner*—Robert L Nasser
(74) *Attorney, Agent, or Firm*—Virtual Law Partners LLP

(57) ABSTRACT

Systems, devices and methods for monitoring and evaluating cognitive effectiveness are provided. In one exemplary embodiment, a system for monitoring cognitive effectiveness can include a central network communicatively coupled with a local computing device, which can in turn be communicatively coupled with a portable monitoring device. The portable monitoring device can be located in proximity with a subject and configured to collect data from the subject usable in determining a cognitive effectiveness level. Adaptive methods for determining cognitive performance are also provided.

20 Claims, 7 Drawing Sheets

SYSTEMS AND METHODS FOR MONITORING AND EVALUATING INDIVIDUAL PERFORMANCE

FIELD OF THE INVENTION

The present invention relates generally to the remote monitoring of individual performance with distributed systems and evaluating the monitored performance.

BACKGROUND OF THE INVENTION

Recently, societal trends have indicated that a sizable portion of the population have been and will continue to suffer from sleep deprivation. Although much research has been performed on the causes of and potential remedies for sleep deprivation, research into the effects of sleep deprivation on the cognitive performance of an individual has been relatively more limited.

Much of the research into the effect of sleep loss on cognitive effectiveness has been directed towards algorithmic techniques for correlating sleep and wake states with cognitive effectiveness levels. U.S. Pat. No. 6,241,686 (hereinafter "Balkin") entitled "System and Method for Predicting Human Cognitive Performance Using Data from an Actigraph" and U.S. Pat. No. 6,579,233 (hereinafter "Hursh") entitled "System and Method for Evaluating Task Effectiveness Based on Sleep Pattern" each propose algorithmic techniques for correlating sleep loss with cognitive effectiveness and making past or future predictions of cognitive performance based, generally, on measured sleep and wake states and are fully incorporated by reference herein.

In addition to the algorithmic techniques, these and other references propose systems for measuring the sleep and wake states of an individual, performing analysis of this measured data and presenting the results to a user. However, these approaches lack the capability to adapt sufficiently to variations between individual users, fail to present data to users in a fully comprehensive manner, and suffer from inefficient data collection and analysis techniques.

Accordingly, improved devices, systems and methods for monitoring and evaluating individual performance are needed.

SUMMARY

Improved devices, systems and methods for monitoring and evaluating individual performance and the like, are provided in this section by the way of exemplary embodiments. These embodiments are examples only and are not intended to limit the invention.

In one exemplary embodiment, a method of monitoring individual performance is provided that includes measuring a objective data parameter corresponding to a first aspect of a subject, collecting a subjective data parameter corresponding to a second aspect of the subject by way of a user interface, and determining a cognitive effectiveness level of the subject based at least on the objective and subjective data parameters.

The determined cognitive effectiveness level can be one of a past, current or future cognitive effectiveness level. Also, the cognitive effectiveness level can be determined with a cognitive effectiveness determination algorithm.

The objective data parameter can be any of multiple types of parameters. In one embodiment the objective data parameter can be representative of the subject's physical motion, such as an actigraph data parameter, while in another embodiment the objective data parameter can be a parameter representative of a blood oxygen level of the subject. In yet another exemplary embodiment, the objective data parameter can be a near infrared spectroscopy (NIRS) signal parameter.

The subjective data parameter can be any of multiple types of parameters. In one embodiment, the subjective data parameter can be a data parameter representative of a subject's manual indication of a subjective mental state, such as a wake state and the like. In another exemplary embodiment, the subjective data parameter can be a response to a test input by the subject.

In another exemplary embodiment, the cognitive effectiveness level of the subject can be determined based on at least the objective data parameter, and the determined cognitive effectiveness level can be adjusted based upon the collected subjective data parameter. For instance, the subjective data parameter can correspond to a wake state and the boundary of the wake state can be adjusted based upon the collected subjective data parameter and a new cognitive effectiveness level can be determined therefrom.

In another exemplary embodiment, the cognitive effectiveness level of the subject can be determined by inputting the objective and subjective data parameters into a cognitive effectiveness determination algorithm.

In another exemplary embodiment, the method can further include collecting an individual characteristic data parameter corresponding to a third aspect of the subject and determining the cognitive effectiveness level of the subject based at least on the objective, subjective and individual characteristic data parameters. The individual characteristic data parameter can be a gender of the subject, a racial origin of the subject, a genetic characteristic of the subject and the like.

In another exemplary embodiment, the cognitive effectiveness level can be determined with a cognitive effectiveness determination algorithm and the cognitive effectiveness determination algorithm can be adapted to the traits of the subject. The adaptation can include altering a population-level based cognitive effectiveness determination algorithm into a subject-based cognitive effectiveness determination algorithm.

Other devices, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, both as to its structure and operation, maybe gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION

Figure 1:
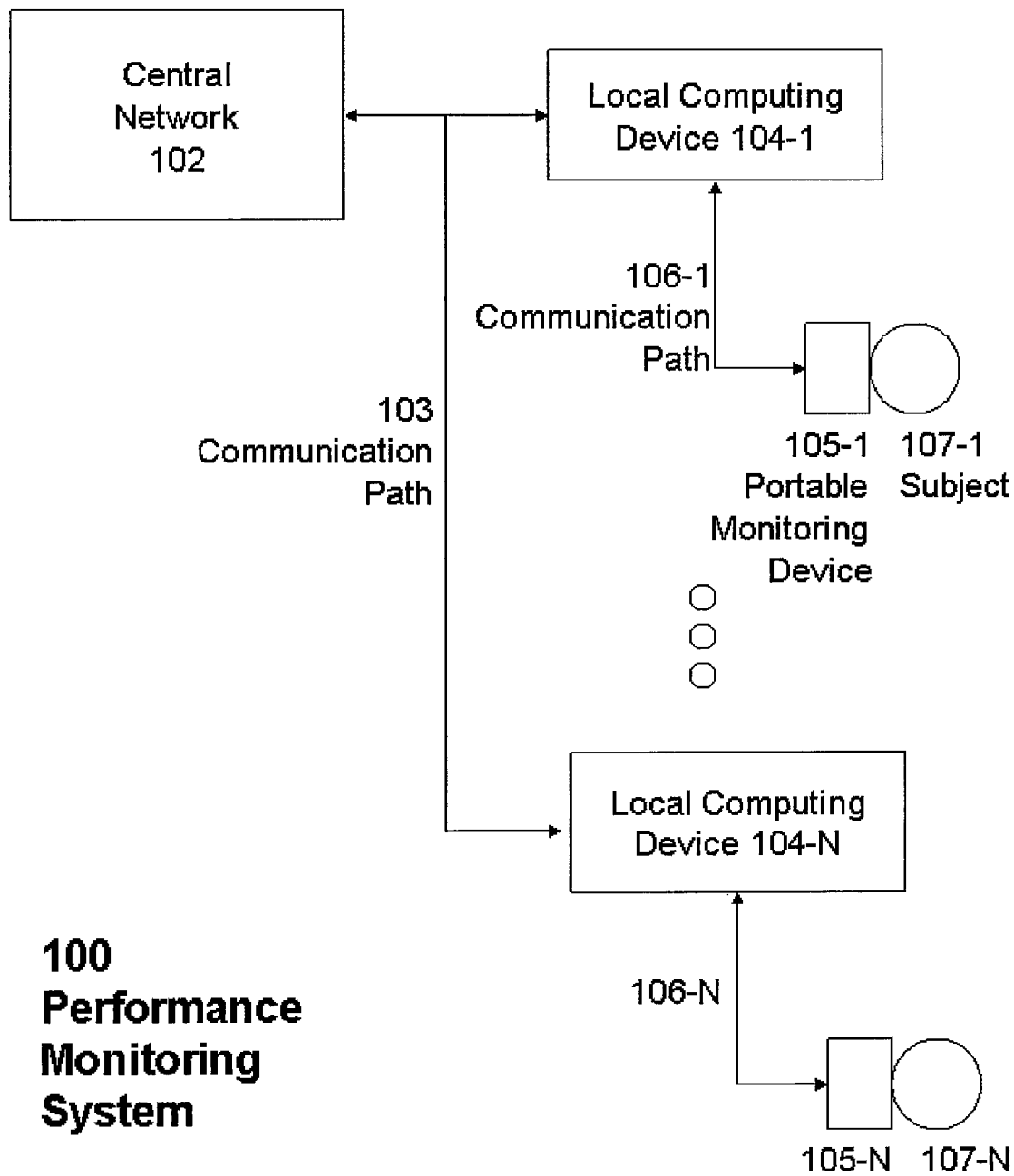
FIG. 1 is a block diagram depicting an exemplary embodiment of a performance monitoring system.

Provided herein are improved systems and methods for monitoring and evaluating individual performance including, but not limited to, individual cognitive performance. FIG. 1 is a block diagram depicting an exemplary embodiment of performance monitoring system 100. Performance monitoring system 100 is a distributed system capable of monitoring the performance of one or more individual subjects at different physical locations. System 100 preferably includes a central network 102 in communication with one or more local computing devices 104-1 through 104-N, preferably by way of a public or private communication path 103, such as the internet. It should be noted that N can be any number desired. Local computing devices 104-1 through 104-N are in communication with a portable monitoring device 105-1 through 105-N by way of a communication path 106-1 through 106-N, respectively, as depicted here. Each communication path 106 is preferably a wireless communication path, although wired communication can be used as well. Each portable monitoring device 105 is preferably physically coupled to an individual subject 107 to be monitored. Each of communication paths 103 and 106 can be bidirectional to allow for data transfer between each of the devices within system 100. Furthermore, a single local computing device 104 can also communicate with multiple portable monitoring devices 105 if desired.

In one exemplary embodiment, system 100 operates to monitor cognitive effectiveness of the various subjects 107-1 through 107-N. For instance, portable monitoring device 105-1 can collect data from corresponding subject 107-1 and communicate that data to the corresponding local computing device 104-1 by way of communication path 106-1. Local computing device 104-1 can then assemble the data reported from portable monitoring device 105-1, process and format the assembled data and communicate the resulting data to central network 102 by way of communication path 103. Central network 102 can then further analyze the data and output a cognitive effectiveness level for subject 107-1 back to local computing device 104-1 or any other desired location.

In the embodiment depicted here, portable monitoring device 105 is preferably configured to collect one or more data parameters that correspond to one or more physiological aspects of subject 107. This data parameter, or set of data parameters, is preferably capable of being used to determine (or predict) a past, present or future cognitive effectiveness level. The collected data parameter can be any data parameter usable to determine cognitive effectiveness including, but not limited to, activity data, sleep/wake data, event data, objective data, and subjective data (e.g., data generated from direct user input).

In one exemplary embodiment, these data parameters can be representative of the subject's sleep/wake state at a given moment in time, i.e., whether the subject is awake or asleep at a given moment in time. These data parameters can be classified as being objectively or subjectively derived. These data parameters can then be used to determine a cognitive effectiveness level, which is an estimated quantification of the relative amount of cognitive ability, such as decision-making ability, which subject 107 can expect to have at a given moment in time—before, during or after collection of the data parameter.

Figure 2A:
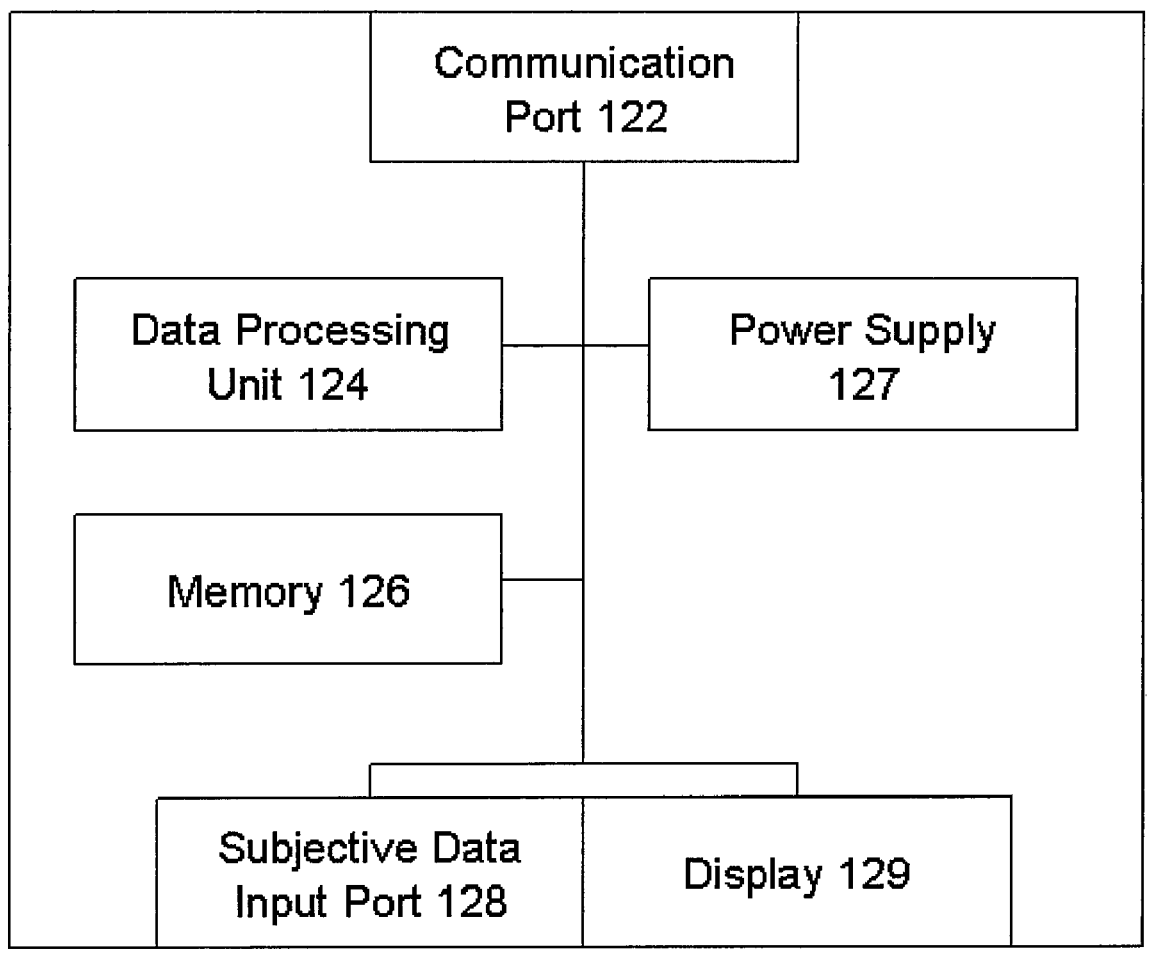
FIG. 2A is a block diagram depicting an exemplary embodiment of a portable monitoring device.

FIG. 2 is a block diagram depicting an exemplary embodiment of portable monitoring device 105. In this embodiment, portable monitoring device 105 can include a sensor 120 configured to collect data and a communication port 122 configured to communicate the collected data to another device, preferably local computing device 104. Portable monitoring device 105 can also include a data processing unit 124, a bus 125, a memory 126, a power supply 127, a subjective data input port 128, and/or a display 129.

Portable monitoring device 105 can collect data of any desired physiological aspect in any desired manner. For instance, in one exemplary embodiment, portable monitoring device 105 can collect physiological data representative of the motion level of subject 107 with sensor 120 configured as an actigraph. The collected motion level data can then be correlated to a current sleep/wake state of subject 107 with an appropriate algorithmic technique, such as the Cole-Kripke algorithm (described in "Automatic Sleep/Wake Identification from Wrist Actigraphy" published in Sleep, vol. 15, pp. 461-469 (1992)) and other algorithms, not limited to those based on the number of zero-crossings detected by the actigraph. Subsequently, the sleep/wake state can be used to determine a cognitive effectiveness level of subject 107 using an appropriate algorithmic technique, such as the techniques described in the Hursh or Balkin references above.

In another exemplary embodiment, portable monitoring device 105 can collect other physiological data representative of physiological aspects of subject 107 including, but not limited to biometric data such as heart rate, breathing rate, blood pressure, skin temperature, galvanic skin response, blood oxygenation level, brain and/or nervous system electrical activity level and the like. In one exemplary embodiment, sensor 120 is configured as an infrared sensor, such as a near infrared spectroscopy (NIRS) sensor. In this embodiment, NIRS sensor 120 can collect physiological data, such as blood oxygenation levels, breath rate, heart rate and other data that can then be used to determine a cognitive effectiveness level. An embodiment that implements NIRS sensor 120 will be described in more detail below.

Portable monitoring device 105 is preferably configured to be wearable on subject 107, although device 105 can also be placed in proximity with subject 107 without making actual physical contact, if desired. Portable monitoring device 105 can also be implantable if desired. When configured to be wearable, portable monitoring device 105 can be worn around the wrist, ankle, neck, or head, or worn on any other part of the body as desired.

As mentioned above, portable monitoring device 105 is preferably configured to communicate with local computing device 104 by way of communication port 122. This communication can occur in real-time as data is collected, at predetermined intervals, as a result of prompting by local computing device 104, any combination thereof or otherwise. Communication port 122 can be configured to communicate externally in any desired manner. In one exemplary embodiment, port 122 is configured to communicate wirelessly using IEEE 802.11, Bluetooth, ZigBee, any mobile communication standard (e.g., WCDMA, GSM etc.), infrared communication and the like. In another exemplary embodiment, port 122 is configured as a wired port, such as a universal serial bus (USB) port, an IEEE 1394 FireWire port, and the like.

As mentioned above, portable monitoring device 105 can include subjective data input port 128 and display 129. Subjective data input port 128 can be any device used to input data including, but not limited to, a button, switch, rollerball, trackball, wheel/button combination, touchscreen, touchpanel, keyboard, any combination thereof and the like. Furthermore, display 129 can be any type of display including, but not limited to a cathode ray tube (CRT), liquid crystal display (LCD), light emitting device (LED), any combination thereof and the like. Also, port 128 and display 129 can be combined such as in a touchscreen display. Of course, one of skill in the art will appreciate that certain configurations are preferable given the preferred configuration of device 105 as being portable. Thus, the configuration for port 128 and display 129 preferably takes into account weight, size and space in the actual implementation.

As will be described in more detail below, port 128 and display 129 can be used to enter subjective data. The subjective data can indicate subject 107's current mental state, including a sleep/wake state, subject 107's self-appraised cognitive effectiveness level, answers input by subject 107 to cognitive effectiveness tests, such as tests of reaction time, comprehension and/or memory, as well as other types of subjective data that will be appreciated by one of ordinary skill in the art.

Local computing device 104 is configured to communicate with portable monitoring device 105 and preferably includes a processing unit and a user interface. Local computing device 104 is preferably a personal desktop or notebook computer, but can also be a handheld computing device such as a personal digital assistant (PDA), a personal email device (e.g., a BLACKBERRY), a mobile phone, any combination thereof and the like. Local computing device 104 preferably receives data collected by portable monitoring device 105 and processes it into a desired format. This processing can include data conditioning, data filtering, encryption, and/or compression. Local computing device 104 can be configured to send the formatted data to central network 102.

Central network 102 preferably includes a processing unit configured to process the formatted data from local computing device 104 into a cognitive effectiveness level. A data analyst can manually monitor and process data received at central network 102, or all data monitoring and processing can be performed automatically. Once the data has been processed into the desired format, the data can be sent back to subject 107 for assessment or can be sent to a third party (embodiments involving a third party will be discussed in more detail below).

It should be noted that the division of data processing between central network 102, local computing device 104 and portable monitoring device 105 can be organized in any manner desired. For instance, the bulk of data processing can be performed at central network 102 if desired, with local computing device 104 acting as an intermediary to transfer data from portable monitoring device 105 to central network 102. Alternatively, the bulk of data processing can be performed on either portable monitoring device 105 or local computing device 104, with communication with central network 102 for the purpose of data processing avoided altogether.

For instance, in one exemplary embodiment, raw actigraphy data can be collected in the form of a zero-crossing count. This information can then be stored in memory on portable monitoring device 105, where it can be time-stamped and transmitted at a predetermined interval. Local computing device 104 can then receive the data, compile it into tabular format, store a back-up copy of the raw data, compress the data, condition the data, encrypt the data, and transmit the modified actigraphy data along with any other data, such as subjective data and other data entered into local computing device 104 (such as travel information, event start time, event end time, individual-specific pieces of data such as age, sex or location, and the like) to central network 102 where this data is input to the cognitive effectiveness determination algorithm (such as the algorithm described in the Hursh or Balkin references, which are incorporated above).

Similarly, the evaluation or assessment of the cognitive effectiveness level can be performed in any manner desired. In one exemplary embodiment, subject 107 can evaluate the cognitive effectiveness data through a user interface located on local computing device 104, or through display 129 located on portable monitoring device 105. A software tool can be used to facilitate presentation of the cognitive effectiveness data to subject 107. One exemplary tool is the Fatigue Analysis Software Tool/Fatigue Avoidance Scheduling Tool (FAST), described in published U.S. patent application Ser. No. 2003/0018242, entitled "Interface for a System and Method for Evaluating Task Effectiveness Based on Sleep Pattern," which is fully incorporated by reference herein.

Figure 3A:
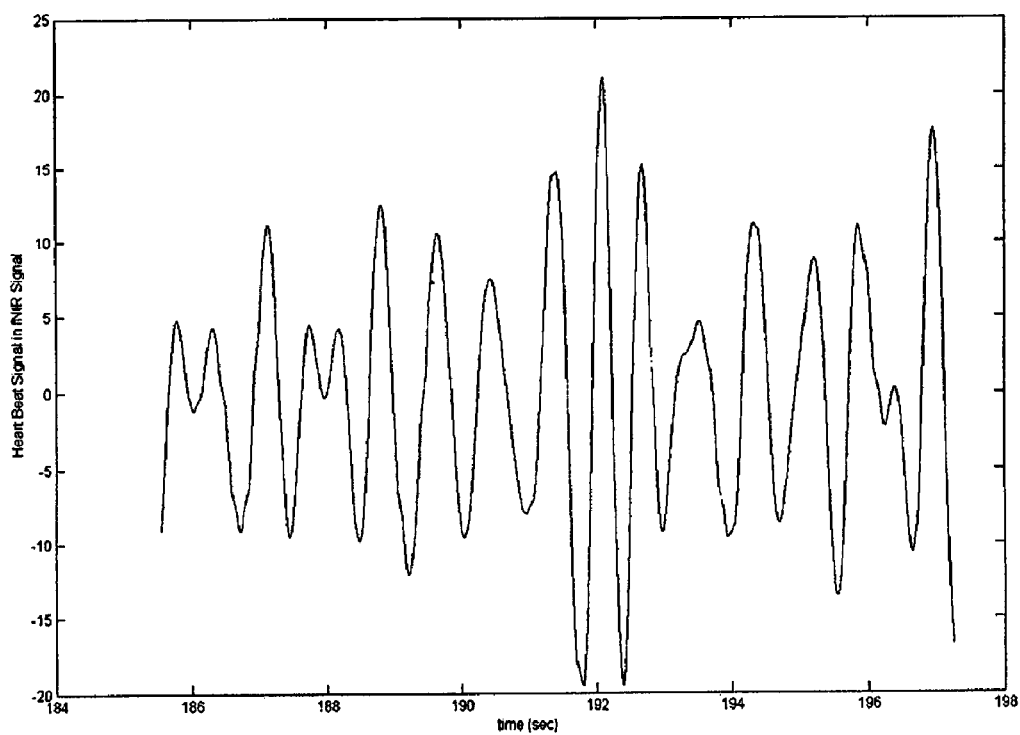
FIGS. 3A-B are exemplary graphs of cardiac and respiratory cycles, respectively, derived from data collected by an exemplary embodiment of the portable monitoring device.
Figure 3B:
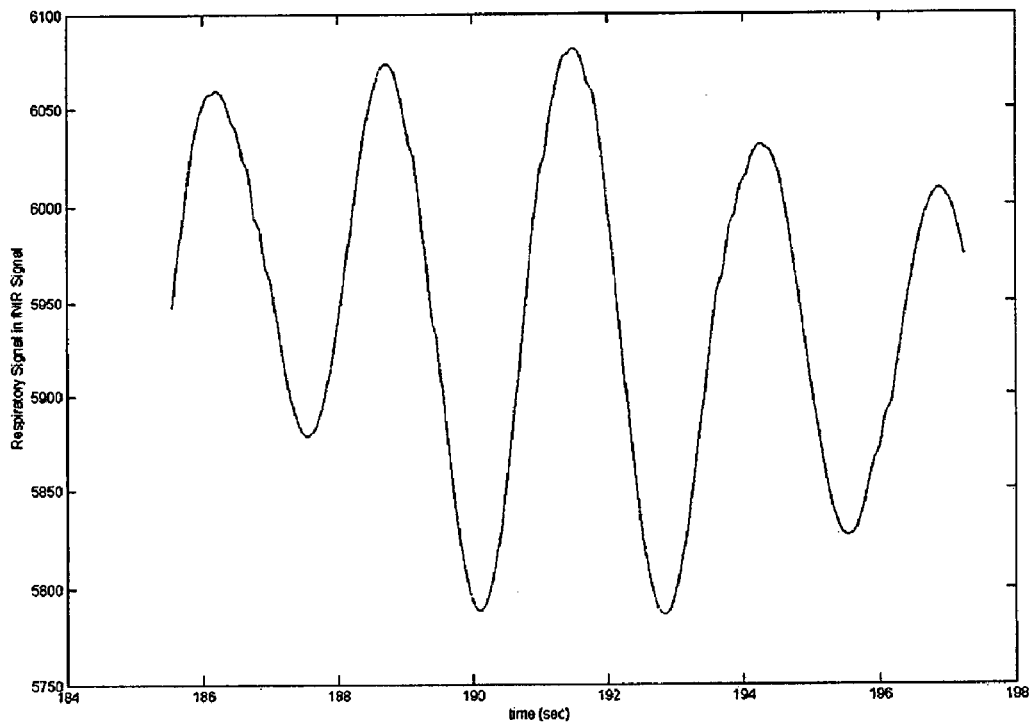

As mentioned above, portable monitoring device 105 can be configured to monitor physiological aspects of subject 107 with an NIRS sensor 120. In one exemplary embodiment, NIRS sensor 120 is configured to measure the oxy- and deoxy-hemoglobin concentrations in subject 107's blood with NIRS. From this NIRS signal, other physiological signals can be obtained or derived. For instance, the dominant measured NIRS signals can include signal oscillations from each heart and respiratory cycle. These signal oscillations can cause rises and drops in the NIRS signal, corresponding to each heart beat and breath taken by the subject. These signal oscillations are overlaid on the raw NIRS signal and can be extracted using filtering. The heartbeat signal, extracted through a band-pass filter, is depicted in the exemplary graph of FIG. 3A. The respiratory signal, extracted through a lowpass filter from the same data, is depicted in the exemplary graph of FIG. 3B, with the same time window as in FIG. 3A. The signals of FIGS. 3A-B can be used to determine the heart and respiratory rates, respectively, of subject 107. This processing can occur in any desired processing unit within system 100.

The heartbeat signal can be used to derive a heart rate variability (HRV) signal. In one exemplary embodiment, the HRV signal is derived through a peak detection algorithm and outlier removal based on an estimated change in heart rate between consecutive beats. The HRV signal is then spectrally analyzed using a fast fourier transform (FFT). Spectral analysis of the HRV signal has been shown to reveal indicators of sleep onset and fatigue levels, after the removal of motion artifacts from the received optical signal, preferably through artifact removal algorithms.

Figure 3C:
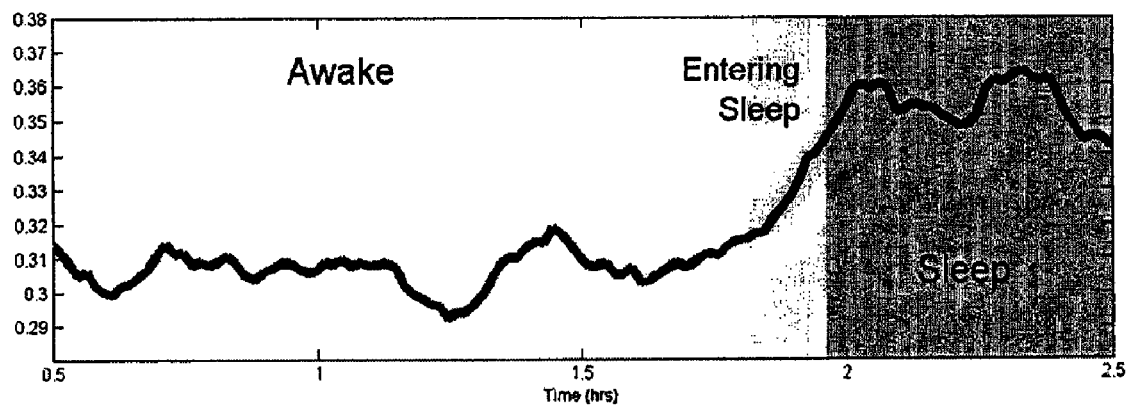
FIGS. 3C-D are exemplary graphs of spectral data derived from cardiac cycle data collected by an exemplary embodiment of the portable monitoring device.
Figure 3D:
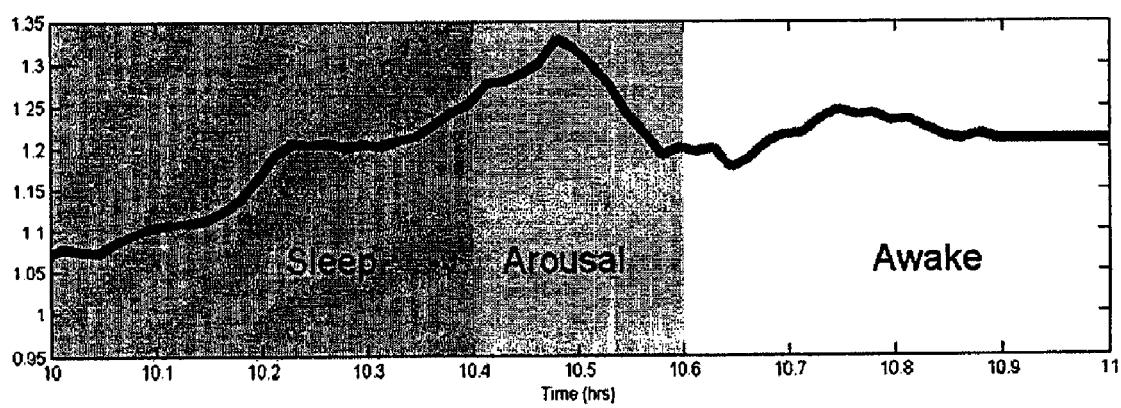

FIGS. 3C-D are exemplary graphs depicting spectral data from the HRV signal derived from heart rate data. This spectral data shows expected changes due to sleep onset and arousal. FIG. 3C depicts an expected increase in the high frequency variance (HFV) of the HRV signal due to the onset of sleep. FIG. 3D depicts the expected peak in the low frequency variance (LFV) due to an arousal from sleep. Respiratory rate can be derived from the NIRS signal as well and can be used to reveal indicators of sleep onset and arousals, if desired.

In addition to collecting objective data representing a physiological aspect of subject 107, system 100 can be configured to collect subjective data as well, and determine cognitive effectiveness based on both the collected objective and subjective data. In one exemplary embodiment, objective data collected by sensor 120 is processed and correlated to a sleep/wake state of subject 107 using a sleep/wake state determination algorithm, and then processed to determine a cognitive effectiveness level using a cognitive effectiveness determination algorithm. Portable monitoring device 105 can be configured to allow subject 107 to manually input an indication that subject 107 is awake through subjective data input port 128. Subject 107 can be prompted to enter subjective input by device 105 or subject 107 can enter subjective input voluntarily. This subjective data can be used to verify the sleep/wake state that was determined based on the objective data. If a discrepancy exists, the bounds for the sleep/wake state can be modified accordingly to yield a more accurate cognitive effectiveness prediction.

System 100 can also be configured to collect subjective data relating to the cognizant state of subject 107 at a given point in time. This data can be collected through a cognitive effectiveness test that evaluates subject 107's ability to perform tasks of varying degrees of difficulty. Examples can include tests of subject 107's reaction time, ability to comprehend relatively complex information, short term memory, long term memory and the like. These tests can be administered through the local computing device 104, through the portable monitoring device 105, or through other devices. The results of the test or tests can be reported to system 100 and used verify the accuracy of subject 107's current predicted cognitive effectiveness level or the test results can be used to directly predict subject 107's cognitive effectiveness level at a past, current or future point in time.

Also, correlation can be performed with the objective data to adjust the sleep/wake determination algorithm to attempt to eliminate future discrepancies. For instance, if the sleep/wake determination algorithm incorrectly predicts a sleep state based on certain objective data characteristics, the algorithm can be modified, or tuned, to more accurately predict sleep/wake states in the future. As a result, system 100 can be configured to dynamically adapt to the characteristics of each individual subject 107. Preferably, this is an iterative process that continues over time, in order to continually adapt the algorithm to the characteristics of the individual subject 107.

For instance, in another exemplary embodiment, system 100 can be configured to implement an adaptive algorithm by first measuring activity with actigraph sensor 120 and determining a corresponding sleep/wake state based on the Cole-Kripke algorithm. Sleep scores are assigned to epochs of uniform time period based on the collected objective actigraph data. Subjective data, when available, can be used to modify the bounds for sleep and wake periods. The subjective data can be stored and used to individually optimize the Cole-Kripke algorithm parameters and weights for a given subject 107.

Figure 4:
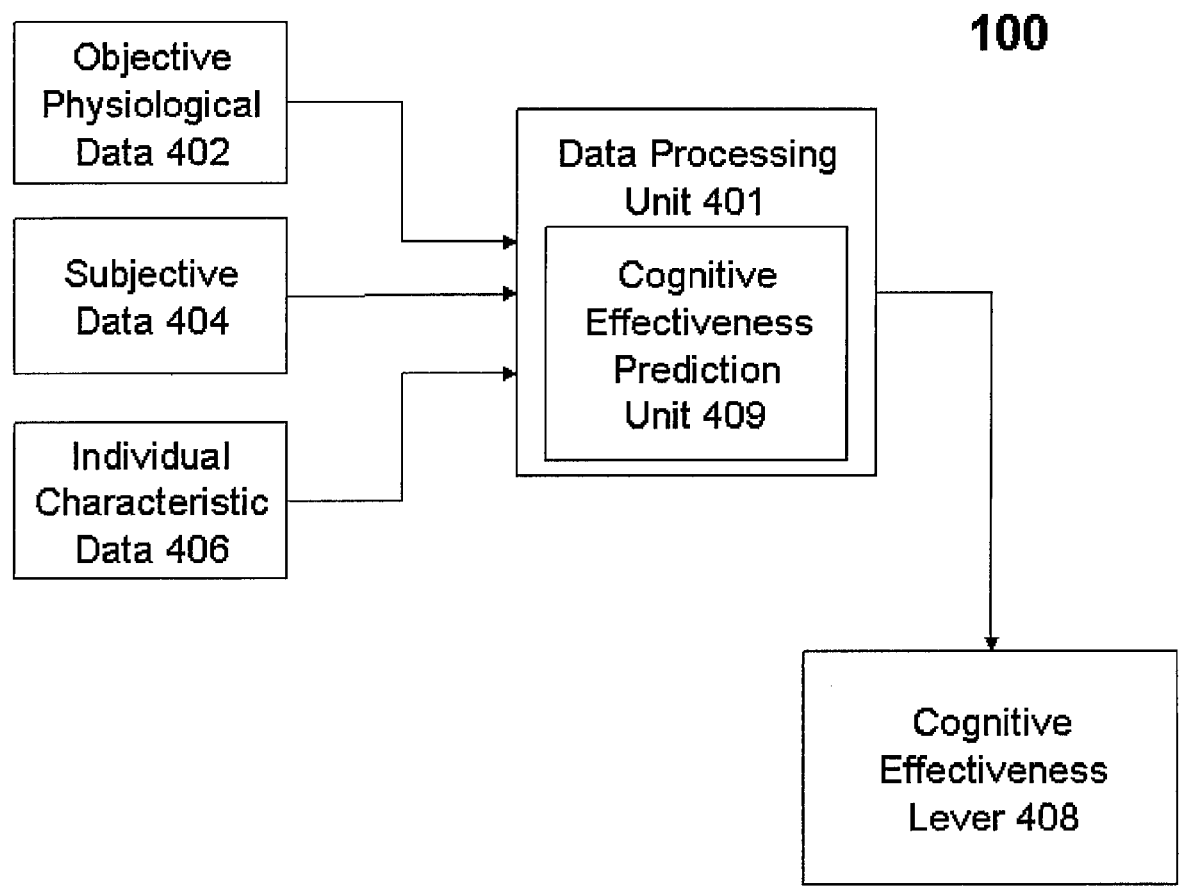
FIG. 4 is a functional block diagram depicting another exemplary embodiment of a performance monitoring system.

In another exemplary embodiment, a host of physiological aspects and other individual-specific characteristics are used to adaptively improve the accuracy of the cognitive effectiveness predictions over time. FIG. 4 is a functional block diagram depicting an exemplary embodiment of system 100 configured for algorithmic adaptation. Here, system 100 includes a processing unit 401, which can be located anywhere throughout system 100 (if implemented in portable monitoring device 105, processing unit 401 would be equivalent to processing unit 124). Here, processing unit 401 includes a cognitive effectiveness prediction unit 409 that is configured to use a customizable population-level model for predicting a cognitive effectiveness level 408. In this embodiment, objective physiological data 402, subjective data 404, and/or individual characteristic data 406 are each collected and input into processing unit 401, for use by cognitive effectiveness prediction unit 409.

Objective physiological data 402 can be any data relating to the measurable aspects of the body of subject 107, such as motion/activity data, heart rate, breathing rate, blood pressure, skin temperature, galvanic skin response, blood oxygenation level, brain and/or nervous system electrical activity level and the like. This data 402 is preferably obtained by sensor 120 within portable monitoring device 105.

Subjective data 404 can be any data that is based on a subjective assessment of subject 107. Subjective data 404 is typically input by subject 107, but can also be input by another individual possessing information on the state of subject 107. Subjective data 404 can be data confirming whether subject 107 is currently asleep or awake, data confirming whether subject 107 was asleep or awake at a past point in time, data representative of when subject 107 plans to sleep or wake in the future, data representative of a current or past cognitive effectiveness level of subject 107, data representative of a current or past feeling of exhaustion, feedback data representative of subject 107's evaluation of a previously output cognitive effectiveness level 408 and the like. This data 404 is preferably obtained by subjective input into subjective data input port 128 in portable monitoring device 105 or subjective input into local computing device 104.

Individual characteristic data 406 can be any data that is representative of a broad individual characteristic. Examples can include race, gender, pharmacological data, heritage, genetic traits and the like. This data 406 is preferably obtained by input into subjective data input port 128 in portable monitoring device 105, input into local computing device 104 by subject 104 or input into central network 102 by another party with knowledge of the individual characteristics of subject 107 freely disclosed by subject 107.

Cognitive effectiveness prediction unit 409 is preferably configured to predict a cognitive effectiveness level 408 based on any or all of the input data 402-406 and, also, adapt itself to improve the accuracy of predictions based on any or all of the input data 402-406. In one exemplary embodiment, feedback provided by subject 107 on the accuracy of a current cognitive effectiveness level 408 can be input as subjective data 404 and used by cognitive effectiveness prediction unit 409 to rescale or individually customize the population-level model appropriately to bring further predictions in-line with subject 107's self-assessment. In other words, the population-level model (or algorithm) can be customized, adapted, or individualized into a relatively more subject-based model to improve the accuracy of predictions for a given subject 107. In doing so, the model is no longer optimized to produce accurate predictions for any member of a given population, but is instead optimized for a subset, or even an individual, within the population.

Furthermore, adjustments to the population-level model as well as data 402-406 can be shared with central network 102 and used to correlate changes to the population-level model with specific input data 402-406 to improve the accuracy of the population-level model for other individuals. For instance, based on adjustments made for male and female subjects 107, the population-level model can be customized to take into account the gender of a new subject 107 using system 100 for the first time.

Figure 5:
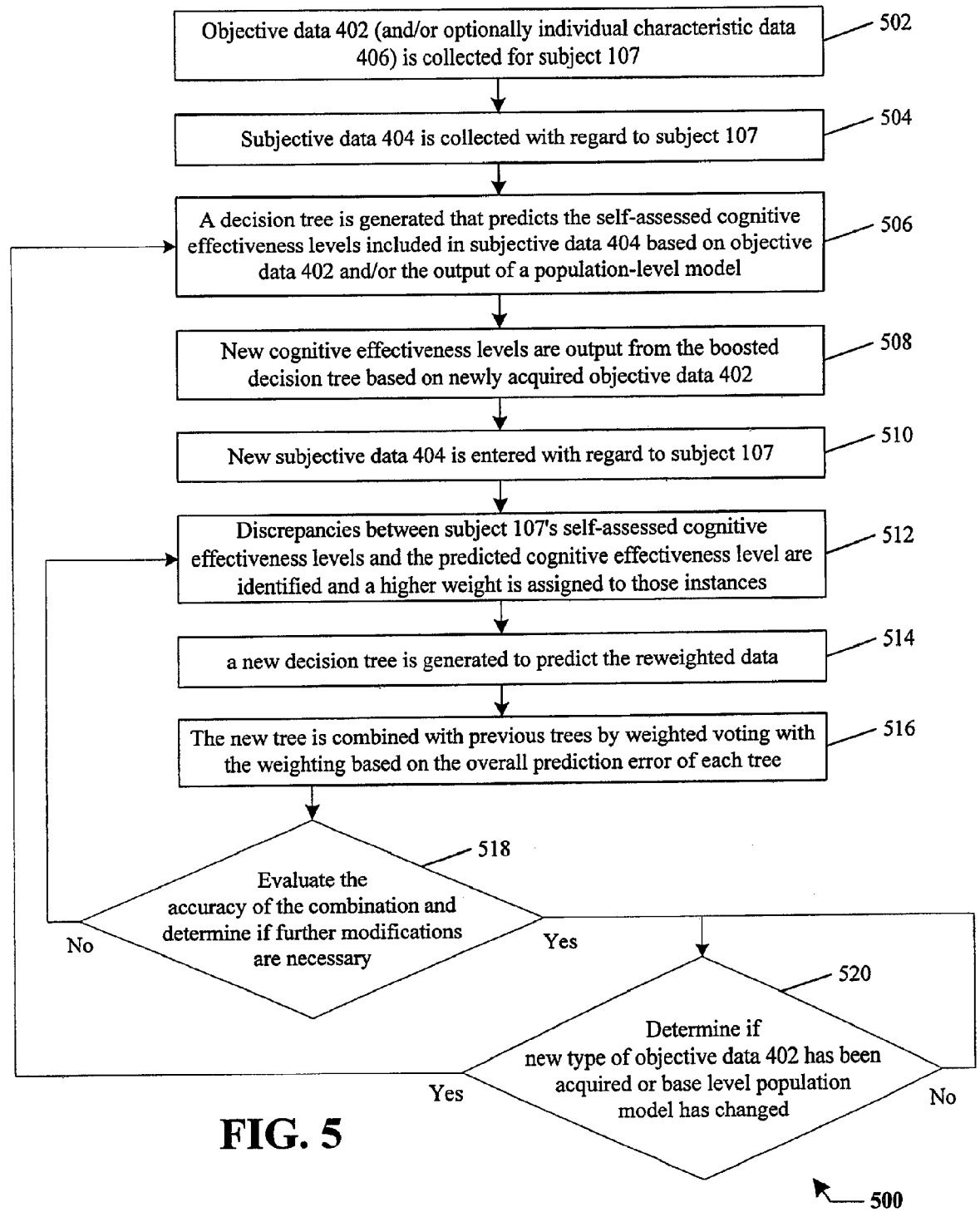
FIG. 5 is a flow diagram depicting an exemplary method of determining a cognitive effectiveness level.

In one exemplary embodiment, cognitive effectiveness prediction unit 408 is configured to use a boosted decision tree technique to adapt the population-level model to a subject-based model for a given subject 107. FIG. 5 is a flow diagram depicting one exemplary method 500 where cognitive effectiveness prediction unit 408 uses a boosted decision tree technique. At 502, objective data 402 (and/or optionally individual characteristic data 406) is collected for subject 107. At 504, subjective data 404 is collected with regard to subject 107. Preferably, subjective data 404 includes self-assessed cognitive effectiveness levels entered by subject 107. At 506, a decision tree is generated that predicts the self-assessed cognitive effectiveness levels included in subjective data 404 based on objective data 402 and/or the output of a population-level model.

At 508, new cognitive effectiveness levels are output from the boosted decision tree based on newly acquired objective data 402 (and/or optionally individual characteristic data 406). At 510, new subjective data 404 is entered with regard to subject 107, preferably including subject 107's self-assessed cognitive effectiveness levels. At 512, discrepancies between subject 107's self-assessed cognitive effectiveness levels and the predicted cognitive effectiveness level output by the decision tree are identified and a higher weight is assigned to those instances. At 514, a new decision tree is generated to predict the reweighted data. At 516, this new tree is combined with previous trees by weighted voting with the weighting based on the overall prediction error of each tree. At 518, the accuracy of the combination is evaluated and if further modifications are necessary, the method reverts to 512. If not, the method proceeds to 520 and waits for new types of objective data 402 (or individual data 406) to be acquired or changes in the base level population model, in which case the method reverts to 506.

In addition to providing a predicted level of cognitive effectiveness, system 100 can be configured to provide behavioral guidance to subject 107 based on the predicted cognitive effectiveness level. The behavioral guidance can be provided in real-time and can inform subject 107 as to the effect current and/or future behavior will have on subject 107's cognitive effectiveness level. As mentioned above, portable monitoring device 105 can include display 129. Portable monitoring device 105 can generate a behavioral guidance message with processing unit 124 (or receive a behavioral guidance message by way of communication port 122) and present the message to subject 107 on display 129. A behavioral guidance message can be generated at pre-determined intervals during certain times of the day, can be generated as a result of prompting by subject 107, can be generated as a result of variations in data collected by sensor 120, or in any other desired manner.

Preferably, the conditions under which a behavioral guidance message should be generated are stored in system 100 as a set of behavioral guidance parameters. The behavioral guidance parameters can include time parameters, date parameters, predicted cognitive effectiveness level parameters, objective data parameters, subjective data parameters, individual characteristic data parameters, interval parameters (i.e., how often should a behavioral guidance message be generated and is this interval fixed or variable dependent on the time of day, date, severity of collected objective or subjective data, etc.) and the like.

In one exemplary embodiment, a behavioral guidance message informs the user as to what consequences sleep time will have on cognitive effectiveness for the next day. For instance, if a set of behavioral guidance parameters are used that specify that should system 100 detect that subject 107 is still awake past a predetermined time of day, for instance, 10 o'clock p.m., system 100 can be configured to generate a behavioral guidance message and display it on portable monitoring device 105. The behavioral guidance message can contain information such as an average cognitive effectiveness level for a specific event or time period in the future subject 107 can expect to achieve if subject 107 goes to sleep within 30 minutes (e.g., 90% of maximum), 60 minutes (e.g., 85% of maximum) and 90 minutes (e.g., 80% of maximum) from the current time, and wakes at a normal time the following day. In such an instance, subject 107 preferably sees a quantified representation of the consequences of continuing to remain awake, through the ever-decreasing predicted cognitive effectiveness levels. Updated behavioral guidance messages can be continually generated at predetermined intervals until system 100 detects that subject 107 has gone to sleep.

Figure 6:
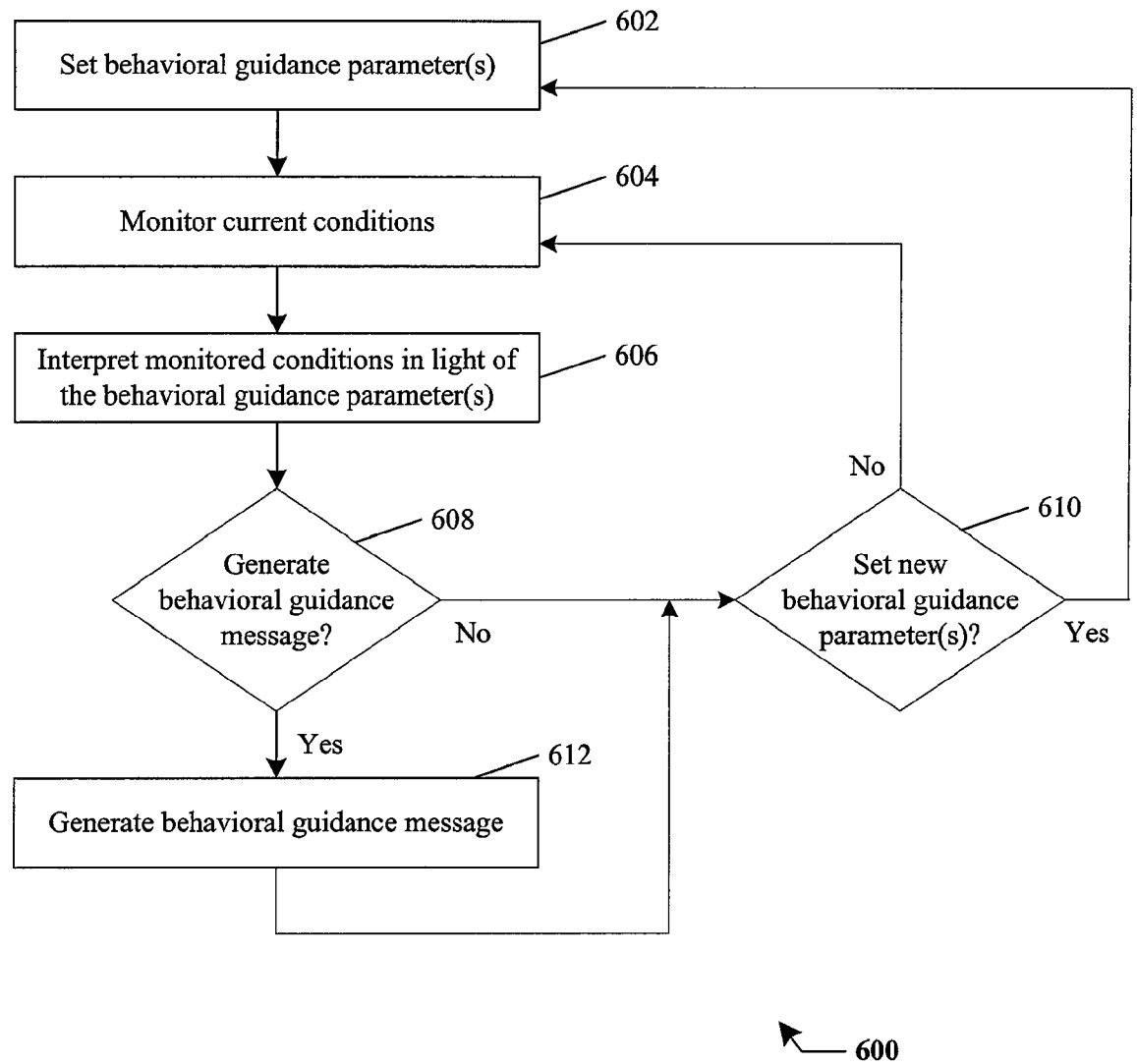
FIG. 6 is a flow diagram depicting an exemplary method of providing behavioral guidance.

FIG. 6 is a flow diagram depicting an exemplary embodiment of a method 600 of providing behavioral guidance, which can be performed with system 100. At 602, one or more behavioral guidance parameters are set. Next, at 604, system 100 monitors the current conditions, which can include collected data (e.g., objective data 402, subjective data 404, and/or individual characteristic data 406) as well as generally known data (e.g., time, day, etc.). Then, at 606, system 100 interprets the monitored conditions in light of the behavioral guidance parameters and, at 608, determines whether the monitored conditions are such that a behavioral guidance message should be generated. If not, then system 100 proceeds to 610 to determine if new behavioral guidance parameters are to be set. If so, system 100 proceeds back to 602 and if not, system 100 proceeds back to 604. If a behavioral guidance message should be generated, then system 100 can proceed from 608 to 612 where the behavioral guidance message is generated. After which, system 100 can proceed to 610 to determine if new behavioral guidance parameters are to be set.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit of the disclosure.

What is claimed is:

1. A method of monitoring individual performance, comprising:
    measuring an objective data parameter corresponding to a first aspect of a subject;
    collecting a subjective data parameter corresponding to a second aspect of the subject by way of a user interface; and
    determining a cognitive effectiveness level of the subject based at least on the objective and subjective data parameters;
    wherein the subjective data parameter is a data parameter representative of a subject's manual indication of a subjective mental state, the subjective mental state including a wake state.

2. The method of claim 1, wherein the determined cognitive effectiveness level is one of a past, current or future cognitive effectiveness level.

3. The method of claim 1, wherein determining a cognitive effectiveness level comprises determining a cognitive effectiveness level with a cognitive effectiveness determination algorithm.

4. The method of claim 1, wherein the objective data parameter is representative of the subject's motion.

5. The method of claim 4, wherein the objective data parameter is an actigraph data parameter.

6. The method of claim 1, wherein the objective data parameter is a parameter representative of a blood oxygen level.

7. The method of claim 6, wherein the objective data parameter is a near infrared spectroscopy signal parameter.

8. The method of claim 1, wherein the subjective mental state is the subject's own mental state.

9. The method of claim 1, wherein the subjective data parameter is a response to a test.

10. The method of claim 1, wherein determining a cognitive effectiveness level of the subject based at least on the objective and subjective data parameters further comprises:
   determining the cognitive effectiveness level of the subject based on at least on the objective data parameter; and
   adjusting the determined cognitive effectiveness level based upon the subjective data parameter.

11. The method of claim 10, wherein the subjective data parameter corresponds to a wake state and adjusting the determined cognitive effectiveness level based upon the subjective data parameter comprises:
   adjusting the boundary of a wake state based upon the subjective data parameter; and
   determining a new cognitive effectiveness level.

12. The method of claim 1, wherein determining the cognitive effectiveness level of the subject based at least on the objective and subjective data parameters comprises inputting the objective and subjective data parameters into a cognitive effectiveness determination algorithm.

13. The method of claim 1, further comprising:
   collecting an individual characteristic data parameter corresponding to a third aspect of the subject; and
   determining the cognitive effectiveness level of the subject based at least on the objective, subjective and individual characteristic data parameters.

14. The method of claim 13, wherein the individual characteristic data parameter is a gender of the subject.

15. A method of monitoring individual performance, comprising:
   measuring an objective data parameter corresponding to a first aspect of a subject;
   collecting a subjective data parameter corresponding to a second aspect of the subject by way of a user interface;
   determining a cognitive effectiveness level of the subject based at least on the objective and subjective data parameters;
   collecting an individual characteristic data parameter corresponding to a third aspect of the subject; and
   determining the cognitive effectiveness level of the subject based at least on the objective, subjective and individual characteristic data parameters wherein the individual characteristic data parameter is a racial origin of the subject.

16. A method of monitoring individual performance, comprising:
   measuring an objective data parameter corresponding to a first aspect of a subject;
   collecting a subjective data parameter corresponding to a second aspect of the subject by way of a user interface; and
   determining a cognitive effectiveness level of the subject based at least on the objective and subjective data parameters;
   collecting an individual characteristic data parameter corresponding to a third aspect of the subject; and
   determining the cognitive effectiveness level of the subject based at least on the objective, subjective and individual characteristic data parameters;
   wherein the individual characteristic data parameter is a genetic characteristic of the subject.

17. A method of monitoring individual performance, comprising:
   measuring an objective data parameter corresponding to a first aspect of a subject;
   collecting a subjective data parameter corresponding to a second aspect of the subject by way of a user interface;
   determining a cognitive effectiveness level of the subject based at least on the objective and subjective data parameters;
   determining the cognitive effectiveness level with a cognitive effectiveness determination algorithm; and
   adapting the cognitive effectiveness determination algorithm to the subject.

18. The method of claim 17, wherein adapting the cognitive effectiveness determination algorithm comprises altering a population-level based cognitive effectiveness determination algorithm into a subject-based cognitive effectiveness determination algorithm.

19. A method for us in monitoring individual performance using an algorithm for determining cognitive effectiveness, comprising:
   measuring at least one objective data parameter corresponding to at least a first aspect of a subject;
   collecting at least one subjective data parameter corresponding to at least a second aspect of the subject by way of at least one user interface; and
   adapting the algorithm for the subject based on at least on the objective data parameter and the at least one subjective data parameter for the subject.

20. The method of claim 19 further comprising:
   collecting at least one individual characteristic data parameter corresponding to at least a third aspect of the subject; and wherein the adapting further includes adapting the algorithm for the subject based on at least on the objective data parameter, the at least one subjective data parameter, and the at least one individual characteristic data parameter for the subject.

* * * * *